United States Patent
Suresh et al.

(10) Patent No.: US 6,241,699 B1
(45) Date of Patent: Jun. 5, 2001

(54) CATHETER SYSTEM AND METHOD FOR POSTERIOR EPICARDIAL REVASCULARIZATION AND INTRACARDIAC SURGERY ON A BEATING HEART

(75) Inventors: Mitta Suresh; Albert Davis, both of Richardson, TX (US)

(73) Assignee: Chase Medical, Inc., Richardson, TX (US)

( * ) Notice: Subject to any disclaimer, the term of this patent is extended or adjusted under 35 U.S.C. 154(b) by 31 days.

(21) Appl. No.: 09/121,151

(22) Filed: Jul. 22, 1998

(51) Int. Cl.[7] ...................................................... A61M 5/00
(52) U.S. Cl. ............................................................... 604/7
(58) Field of Search ............................... 604/4, 506–509, 604/96–99, 101–102, 104, 264, 523, 533; 128/898, DIG. 3; 606/190–92, 194–95

(56) References Cited

U.S. PATENT DOCUMENTS

| | | | |
|---|---|---|---|
| Re. 35,352 | 10/1996 | Peters | 604/4 |
| Re. 35,459 | 2/1997 | Jonkman | 604/164 |
| 2,701,559 | 2/1955 | Cooper . | |
| 3,640,282 | 2/1972 | Kamen et al. | 128/351 |
| 4,129,129 | 12/1978 | Amrine | 128/214 |
| 4,285,341 * | 8/1981 | Pollack | 128/348 |
| 4,328,056 | 5/1982 | Snooks | 156/242 |
| 4,413,989 | 11/1983 | Schjeldahl et al. | 604/96 |
| 4,417,576 | 11/1983 | Baran | 128/207.15 |
| 4,531,936 | 7/1985 | Gordon | 604/49 |
| 4,592,340 | 6/1986 | Boyles | 128/1 D |
| 4,596,552 | 6/1986 | DeVries | 604/44 |
| 4,601,706 | 7/1986 | Aillon | 604/122 |
| 4,610,662 | 9/1986 | Weikl et al. | 604/53 |
| 4,648,384 | 3/1987 | Schmukler | 128/1 D |
| 4,676,778 | 6/1987 | Nelson, Jr. | 604/45 |
| 4,689,041 | 8/1987 | Corday et al. | 604/53 |
| 4,741,328 | 5/1988 | Gabbay | 128/1 D |
| 4,781,682 | 11/1988 | Patel | 604/96 |
| 4,927,412 | 5/1990 | Menasche | 604/96 |
| 4,943,277 | 7/1990 | Bolling | 604/96 |
| 4,988,515 | 1/1991 | Buckberg | 424/529 |
| 5,011,469 | 4/1991 | Buckberg et al. | 604/4 |
| 5,013,296 | 5/1991 | Buckberg et al. | 604/44 |
| 5,021,045 | 6/1991 | Buckberg et al. | 604/53 |
| 5,024,668 | 6/1991 | Peters et al. | 606/194 |
| 5,033,998 | 7/1991 | Corday et al. | 600/18 |
| 5,090,960 | 2/1992 | Don Michael | 604/101 |
| 5,135,474 | 8/1992 | Swan et al. | 604/8 |
| 5,135,484 | 8/1992 | Wright | 604/28 |
| 5,149,330 | 9/1992 | Brightbill | 604/280 |
| 5,151,087 | 9/1992 | Jonkman | 604/164 |
| 5,167,628 | 12/1992 | Boyles | 604/101 |
| 5,171,218 | 12/1992 | Fonger et al. | 604/164 |

(List continued on next page.)

FOREIGN PATENT DOCUMENTS

| | | | |
|---|---|---|---|
| 0 218 275 | 8/1986 | (EP) . | |
| 0 280 25 | 2/1988 | (EP) . | |
| 0 357 338 | 8/1989 | (EP) | A61M/1/36 |
| WO 95/17919 | 6/1995 | (WO) | A61M/25/01 |
| WO 96/30072 | 3/1996 | (WO) | A61M/29/00 |
| WO 96/17644 | 6/1996 | (WO) | A61M/29/00 |

*Primary Examiner*—Sharon Kennedy
*Assistant Examiner*—Catherine Serke
(74) *Attorney, Agent, or Firm*—Haynes and Boone, LLP

(57) ABSTRACT

A catheter system and method of performing posterior epicardial revascularization and intracardiac surgery on a beating heart. Several catheter systems are provided to achieve a left ventricular isolation and a right ventricular isolation as required to facilitate surgery according to the methods of the present invention. Myocardial infusion is provided in either antegrade or retrograde flow to insure the myocardium meets its oxygen demand.

7 Claims, 10 Drawing Sheets

U.S. PATENT DOCUMENTS

| | | | |
|---|---|---|---|
| 5,197,952 | 3/1993 | Marcadis et al. | 604/96 |
| 5,213,576 | 5/1993 | Abiuso et al. | 604/96 |
| 5,221,258 | 6/1993 | Shturman | 604/96 |
| 5,290,231 | 3/1994 | Marcadis et al. | 604/96 |
| 5,308,319 | 5/1994 | Ide et al. | 600/18 |
| 5,308,323 | 5/1994 | Sogawa et al. | 604/95 |
| 5,312,344 | 5/1994 | Grinfeld et al. | 604/101 |
| 5,324,260 | 6/1994 | O'Neill et al. | 604/96 |
| 5,334,142 | 8/1994 | Paradis | 604/53 |
| 5,338,298 | 8/1994 | McIntyre | 604/96 |
| 5,360,403 | 11/1994 | Mische | 604/101 |
| 5,378,230 | 1/1995 | Mahurkar | 604/43 |
| 5,395,330 | 3/1995 | Marcadis et al. | 604/96 |
| 5,395,331 | 3/1995 | O'Neill et al. | 604/96 |
| 5,423,745 | 6/1995 | Todd et al. | 604/53 |
| 5,433,700 | 7/1995 | Peters | 604/4 |
| 5,437,637 | 8/1995 | Lieber et al. | 604/96 |
| 5,443,446 | 8/1995 | Shturman | 604/49 |
| 5,443,448 | 8/1995 | DeVries | 604/96 |
| 5,451,207 | 9/1995 | Yock | 604/53 |
| 5,452,733 | 9/1995 | Sterman et al. | 128/898 |
| 5,458,574 | 10/1995 | Machold et al. | 604/101 |
| 5,458,575 | 10/1995 | Wang | 604/101 |
| 5,478,309 | 12/1995 | Sweezer et al. | 604/4 |
| 5,487,730 | 1/1996 | Marcadis et al. | 604/96 |
| 5,501,667 | 3/1996 | Verduin, Jr. | 604/96 |
| 5,505,598 | 4/1996 | Booth et al. | 604/96 |
| 5,533,957 | 7/1996 | Aldea | 600/16 |
| 5,558,644 | 9/1996 | Boyd et al. | 604/96 |
| 5,571,215 | 11/1996 | Sterman et al. | 623/66 |
| 5,584,803 | 12/1996 | Stevens et al. | 604/4 |
| 5,597,377 | 1/1997 | Aldea | 600/16 |
| 5,609,571 | 3/1997 | Buckberg et al. | 604/4 |
| 5,611,775 | 3/1997 | Machold et al. | 604/53 |
| 5,620,418 | 4/1997 | O'Neill et al. | 604/96 |
| 5,658,311 | 8/1997 | Baden | 606/192 |
| 5,662,620 | 9/1997 | Lieber et al. | 604/280 |
| 5,695,457 * | 12/1997 | St. Goar et al. | |
| 5,807,384 * | 9/1998 | Mueller | 606/7 |

* cited by examiner

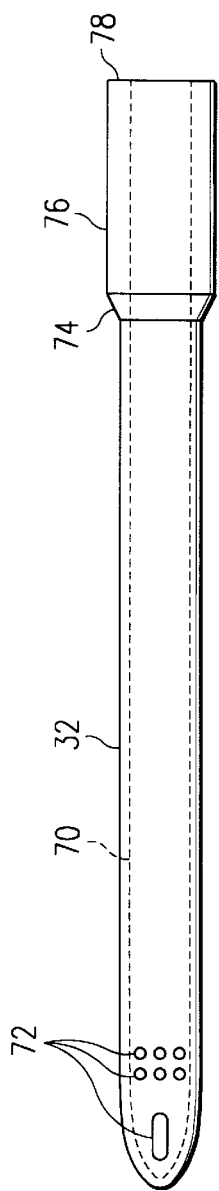
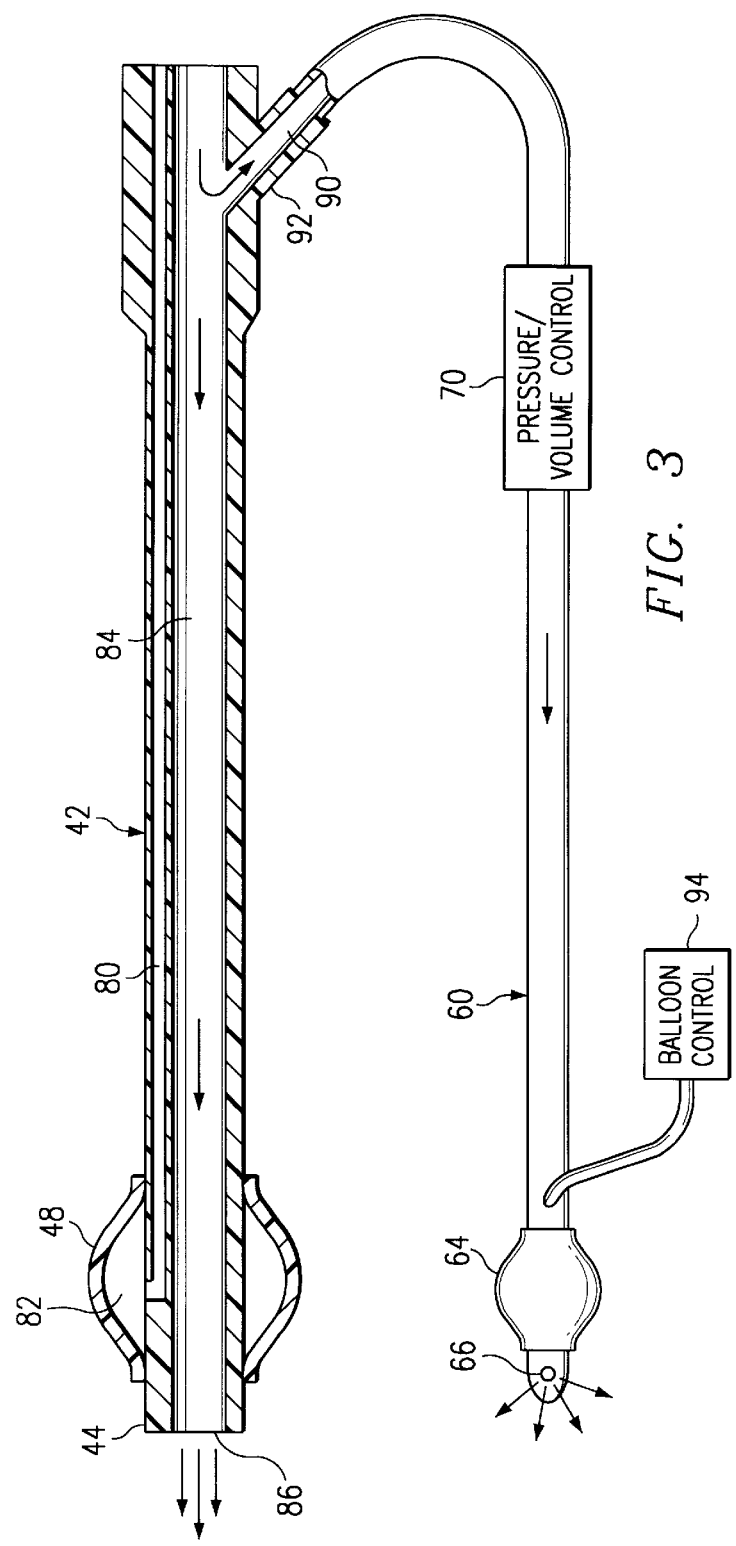
FIG. 2
FIG. 3

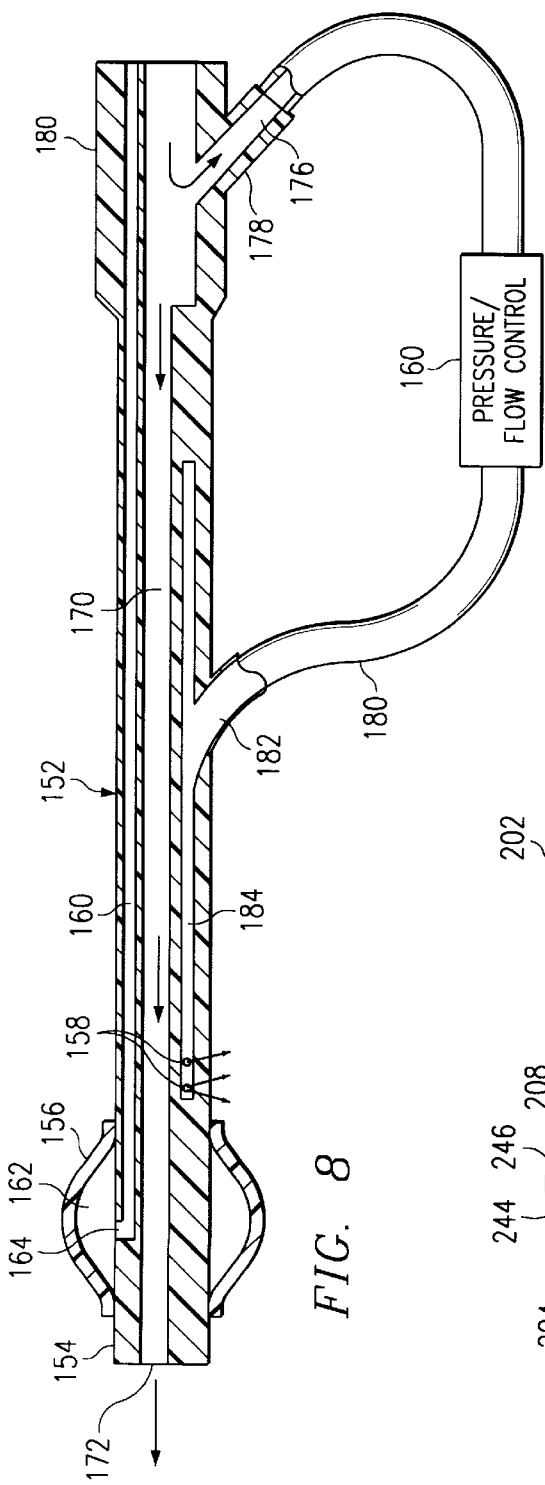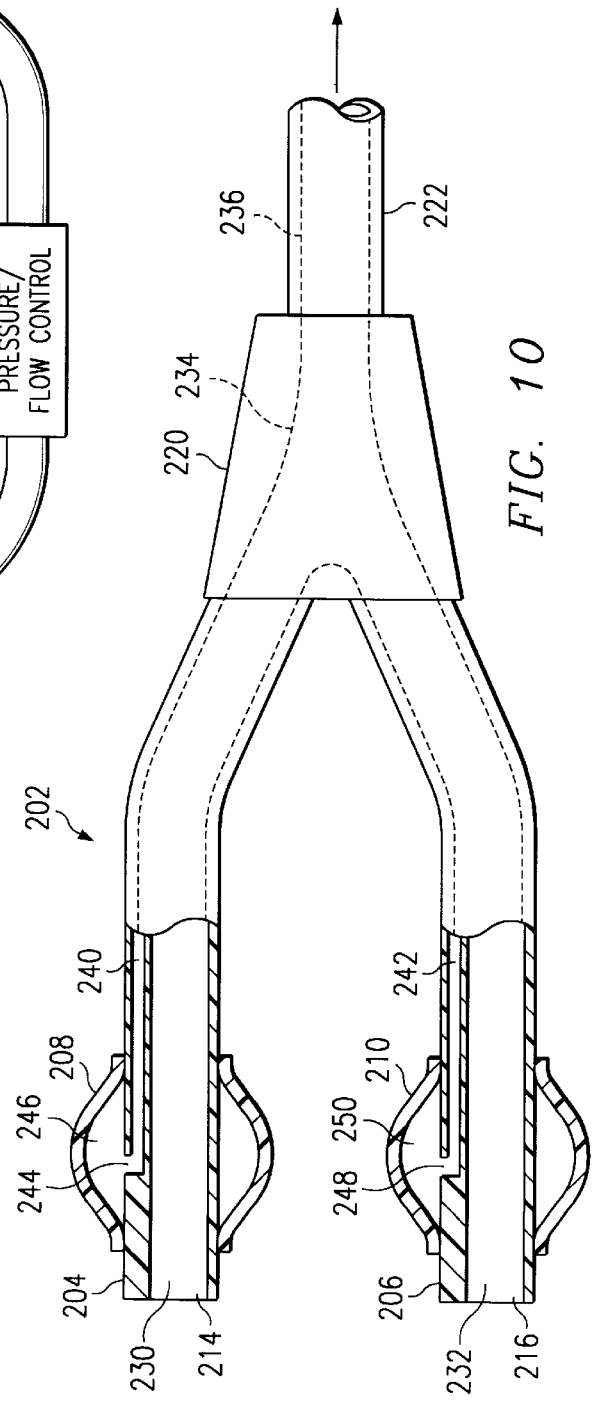

CATHETER SYSTEM AND METHOD FOR POSTERIOR EPICARDIAL REVASCULARIZATION AND INTRACARDIAC SURGERY ON A BEATING HEART

CROSS REFERENCE TO RELATED APPLICATIONS

Cross reference is made to the following commonly assigned patent applications, the teachings of which are incorporated herein by reference:

Integral Aortic Arch Infusion Clamp Catheter, Ser. No. 08/846,666, filed May 1, 1997, Integral Aortic Arch Infusion Clamp Having Pressure Ports, Ser. No. 09/070,696, filed Apr. 30, 1998, Venous Return Catheter Having Integral Support Member, Ser. No. 08/838,802, filed Apr. 10, 1997, and Catheter Having a Lumen Occluding Balloon and Method of Use Thereof, Attorney's Docket 1050-2103, filed Jul. 22, 1998.

FIELD OF THE INVENTION

The present invention is generally related to cardiac catheter systems including venous perfusion and arterial perfusion cardiac catheters for providing cardiopulmonary bypass support and isolation of a heart during heart surgery, and more particularly to a system and method facilitating intracardiac surgery including valvular repair and/or replacement on a beating heart.

BACKGROUND OF THE INVENTION

Use of catheters to administer fluids to and draw fluids out of the body has been a standard practice in medical procedures for years. Multiple catheters may be used to connect an extracorporeal circuit to the body during open-heart procedures. The various catheters are simultaneously or sequentially used to provide different functions, for instance, one catheter for delivering a cardioplegia solution to arrest the heart, with another catheter being inserted into the heart to infuse oxygenated blood to the ascending aorta.

One of the developing technologies in medicine at this time is least invasive cardiac surgery. Currently, the two popular methods of least invasive surgery is either on a beating heart, or on a stable heart. The beating heart surgery is typically limited to anterior epicardial revascularization. Specifically, this surgery includes procedures including anastomosis of the left internal mammary artery (LNIA) to the left anterior descending (LAD) artery.

Left ventricular decompression (LVD) and right ventricular decompression (RVD) are popularly used as assist devices, wherein a pump is used to drain the blood from the left ventricle or the right ventricle and delivered into the aorta or pulmonary artery, respectively, so that the myocardium is rested and can recover over a period of time. Assist devices are popularly used as bridges to heart transplants. In some cases, assist devices are used post-operatively to help the myocardium to recover from the shock of myocardial infarction in combination with the stress of open-heart surgery.

The present invention is directed to a catheter system and method for facilitating intracardiac surgery including valvular repair and/or replacement on a beating heart. It is desirable to keep a heart beating where possible to reduce trauma to the heart. There is a desire for procedures including, repair and/or replacement of the mitrial valve located between the left atrium and the left ventricle, and the aortic valve located at the aortic base of the heart. There is also a desire to provide a procedure to repair the tricuspid valve and the pulmonic valve in the right side of the heart.

SUMMARY OF THE INVENTION

The present invention achieves technical advantages as a catheter system and method facilitating intracardiac surgery on a beating heart. The present invention comprises a catheter system and method for obtaining a left ventricular isolation to drain the left ventricle and facilitate valvular or posterior epicardial surgery on a beating heart including replacement of the mitrial valve and the aortic valve. The present invention also comprises a catheter system and method for obtaining a right ventricular isolation to drain the right atrium and facilitate intracardiac or posterior epicardial surgery on a beating heart, such as to repair the tricuspid valve and the pulmonic valve.

According to a first embodiment of the present invention, a left ventricular isolation is obtained by draining oxygenated blood from the left ventricle of the heart, or draining directly from the pulmonary veins, using a catheter and a pump. The pump directs the drained oxygenated blood to the ascending aorta to provide artrial return. The left ventricle is accessed in one of several ways including a) through the apex of the heart, b) via the pulmonary vein and the mitrial valve, c) via the left atrial apendage and through the mitrial valve, and d) through the aorta and through the aortic valve.

According to a second embodiment of the present invention a right ventricular isolation is obtained by draining the systemic blood from the superior vena cava and the inferior vena cava to provide a bloodless right side of the heart. The drained blood is returned by a pump directly to the pulmonary artery to complete the extracorporeal circuit.

Myocardial infusion is provided while performing the left ventricular isolation and the right ventricular isolation by perfusing the blood vessels of the beating heart in antegrade or retrograde flow. In antegrade flow, a portion of the arterial return blood is infused into the coronaries at the aortic base of the aorta. In retrograde flow, a portion of the arterial return blood is infused into the coronary sinus. In both the antegrade and retrograde flow of myocardial infusion, the perfusion pressures and flow rates are carefully maintained to adequately perfuse the heart to meet the oxygen demand of the myocardium. The pressure and flow rate of the myocardial infusion is carefully controlled to avoid damage to the coronary sinus.

The catheter system of the present invention includes several embodiments for effectively providing a bloodless portion of the heart to facilitate intracardiac surgery on a beating heart. To facilitate repair or replacement of the mitrial valve or aortic valve, for example, several embodiments are provided for draining the left ventricle of the heart. To facilitate repair or replacement of the pulmonic valve and the tricuspid valve on a beating heart, several embodiments are provided to drain the right atrium of the heart.

BRIEF DESCRIPTION OF THE DRAWINGS

FIG. 2 is an illustration of the left ventricle access cannula suited for use in FIG. 1;

FIG. 3 is a cross section of the aortic perfusion cannula of FIG. 1 for providing arterial return of oxygenated blood as well as retrograde myocardial infusion;

FIG. 8 is a cross section of the aortic perfusion catheter of FIG. 7 for providing antegrade myocardial infusion;

FIG. 10 is a partial cross section of one pulmonary vein catheter of FIG. 9 illustrating a pair of distal ends each having a balloon for occluding the respective pulmonary vein as shown in FIG. 9;

DESCRIPTION OF THE PREFERRED EMBODIMENT

Figure 1:
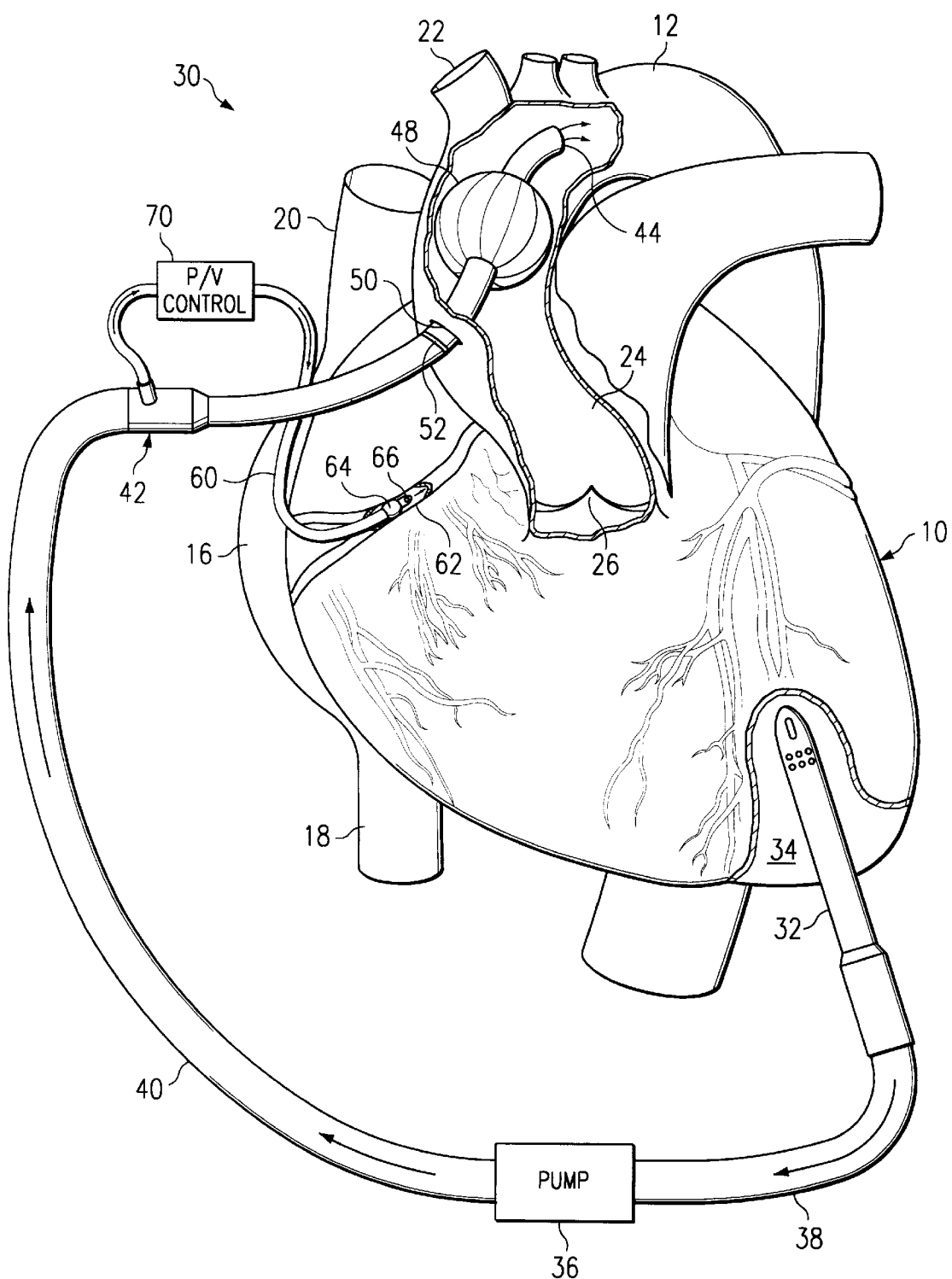
FIG. 1 is an illustration of a first catheter system achieving an left ventricular isolation of the heart to facilitate aortic valve repair/replacement and epicardial surgery whereby blood is drained from the left ventricle via the apex of the heart with retrograde myocardial infusion.

With reference to FIG. 1, there is shown the first preferred catheter system and method of the present invention for facilitating intracardiac surgery and posterior epicardial revascularization on a beating heart. First, to provide a brief overview of the heart to further understand the catheter system and method of the present invention, a brief description of the heart's features will be provided.

A human heart 10 is seen to include an aorta 12, a right atrium shown at 16, with the inferior vena cava being shown at 18 and the superior vena cava being shown at 20. The Brachiocephalie Artery is shown at 22. The aortic base is shown at 24 with the aortic valve being shown at 26.

Referring now to the catheter system 30 shown in FIG. 1, to facilitate repair or replacement of a aortic valve 26 located at the aortic base 24, a left ventricular access cannula 32 is inserted through the apex of the heart to drain oxygenated blood from the left ventricle 34 of the heart to obtain a left ventricular isolation. System 30 is seen to include a pump 36 coupled to the proximal end of catheter 32 via a flexible conduit 38 for draining the left ventricle. Pump 36 has a feedback mechanism responsive to a sensor such as a pressure sensor (not shown) located at the tip of the catheter 32 to ensure the pump drains blood from the left ventricle at a sufficient rate to drain the left ventricle without sucking air into the line. The pump 36 provides the drained blood via a conduit 40 to an aortic perfusion cannula generally shown at 42. Catheter 42 infuses the returned oxygenated blood into the ascending aorta 12 as shown. Returned blood is infused out the distal end 44 of catheter 42 upwardly into the ascending aorta to complete the bypass of the beating heart and perfuse the body. Catheter 42 is further seen to include an inflatable balloon 48 for selectively and effectively occluding the ascending aorta to isolate the distal end of catheter 42 from the aortic base 24. Catheter 42 is inserted into the ascending aorta via an opening 50 created by the physician through the wall of the aorta and is secured thereto using sutures or the like. Catheter 42 further includes a marker or indicia 52 for indicating a proper insertion point of the catheter 42 into the aorta to further assist the surgeon during the proper placement of the catheter distal end within the ascending aorta 12.

The catheter 42 is further seen to include a myocardial infusion catheter portion 60 for providing retrograde flow of oxygenated blood to the coronary sinus 62. Catheter portion 60 has a distal balloon 64 which is selectively and controllably inflated by the physician to occlude the coronary sinus, whereby oxygenated blood is provided in retrograde flow into the coronary sinus via distal opening 66. A pressure and volume control 70 of catheter portion 60 is selectively controlled by the physician to control the volume and pressure of the retrograde infusion flow. For instance, it is typically desired to maintain a volume flow of about 500 milliliters per minute, and a pressure in the range of 40 mm Hg, which is typically not to exceed 60 mm Hg. Catheter portion 60 diverts a small portion of the returned arterial blood to the coronary sinus to insure that the myocardium of the beating heart is sufficiently perfused with oxygenated blood to meet its oxygen demand.

According to the catheter system and method of FIG. 1, posterior epicardial revascularization as well as intracardiac surgery can be provided by the surgeon to repair or replace the aortic valve. This surgery is possible since the heart can remain beating with the left ventricle being isolated and free of blood, and with the myocardium being sufficiently infused. Stabilization platforms currently available in the market can be used to stabilize the specific operational site. The aortic base is rendered essentially bloodless by catheter 32 to facilitate a clear working area for the surgeon while the returned arterial flow is directed into the ascending aorta at a sufficient rate to perfuse the human heart of the patient.

Turning now to FIG. 2, there is shown the left ventricular catheter 32 of FIG. 1. Catheter 32 is seen to be elongated having an inner continuous lumen 70 terminating at a plurality of openings 72 at the distal end thereof. Catheter 32 typically has a continuous diameter along the length thereof to facilitate smooth insertion into the left ventricle 34 of the heart, as shown in FIG. 1. Catheter 32 typically is comprised of a flexible material such as silicone or polyvinylchloride (PVC) or the like. Catheter 32 is further seen to include a transition area 74 in the distal body portion 76 having a distal end 78 adapted to fluidly couple with passageway 38 shown in FIG. 1.

Referring now to FIG. 3, there is shown a partial sectional side view of the aortic perfusion catheter 42 as depicted in FIG. 1. Catheter 42 is seen to include a balloon inflation lumen 80 fluidly communicating with an interior cavity 82 of balloon 48. Lumen 80 facilitates the selective inflation and deflation of balloon 48 as controlled by the surgeon. Catheter 42 is further seen to include a large main lumen 84 having a diameter sufficient to provide adequate oxygenated blood flow at a sufficient pressure to adequately perfuse the human body via distal opening 86 at distal end 44. At the proximal end of catheter 42 is seen a passageway 90 extending through a diverter finger 92 for directing a small portion of the blood flowing through main lumen 84 into the pressure/volume control 70. The small portion of the blood flow communicated via lumen 90 is controlled by control 70 to provide oxygenated blood at a sufficient flow rate and pressure to the distal end of catheter portion 60. The oxygenated blood is dispensed via distal opening 66 for providing retrograde flow into the coronary sinus as shown in FIG. 1. Balloon 64 is controllably inflated by a balloon control 94 so as to properly occlude the coronary sinus 62 without damage thereto. In summary, aortic perfusion catheter 42 provides two functions. First, providing arterial return of oxygenated blood to the ascending aorta 12 to perfuse the body, and second, providing retrograde flow of oxygenated blood to the coronary sinus to provide myocardial infusion.

Figure 4:
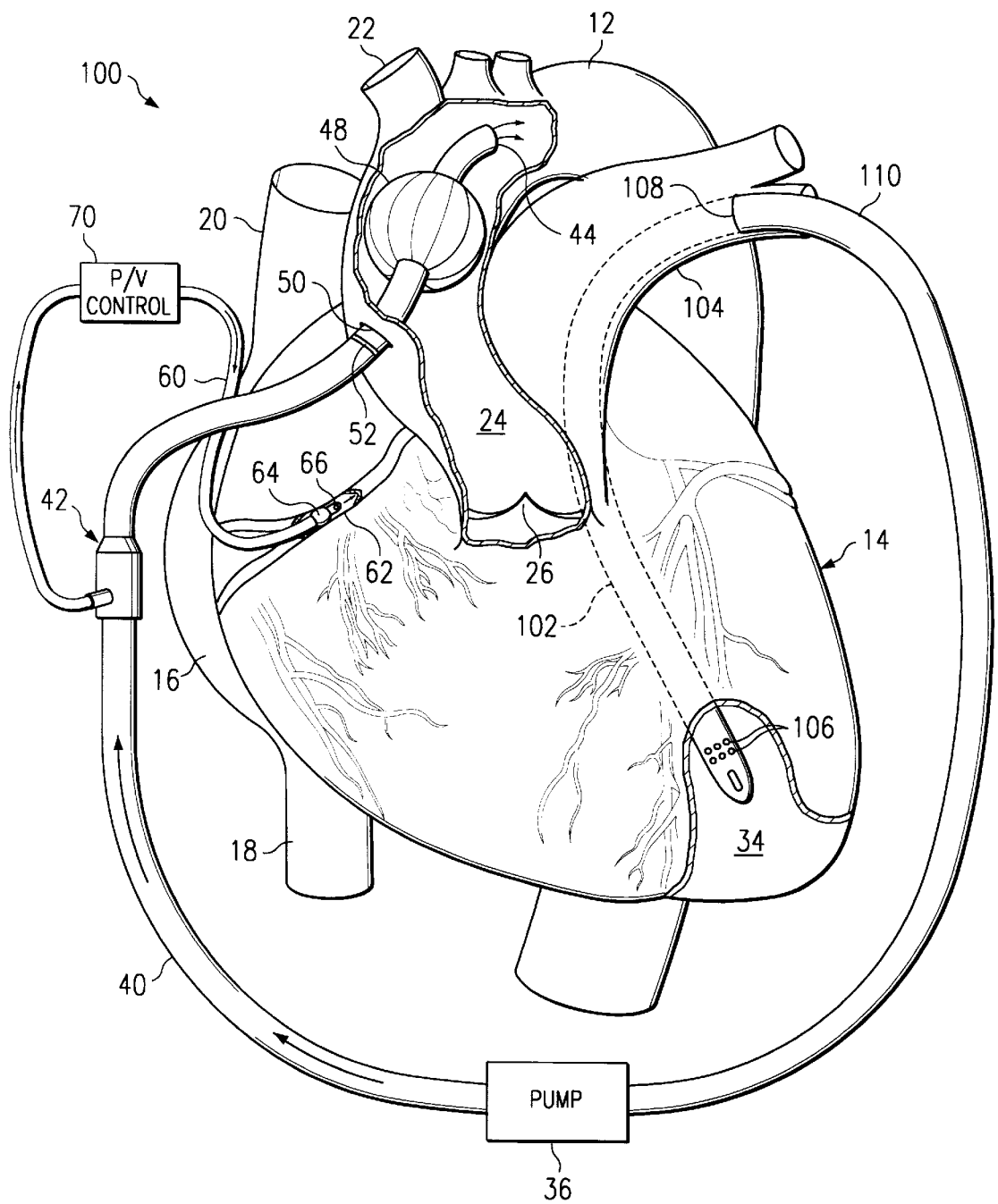
FIG. 4 is an illustration of a second catheter system and method for draining the left ventricle of the heart using a catheter inserted through the right pulmonary vein and the mitrial valve for performing aortic valve replacement/repair and epicardial surgery.

Turning now to FIG. 4, there is shown at 100 a catheter system and method according to a second preferred embodiment of the present invention. The left ventricle 34 is drained using a catheter 102 inserted through the right pulmonary vein 104 and through the mitrial valve to obtain an left ventricular isolation. Catheter 102 is seen to have a plurality of openings 106 at the distal end thereof for draining the left ventricle 34. Catheter 102 is sufficiently flexible to allow maneuvering through an incision 108 created in the right pulmonary vein and manipulation through the mitrial valve into the left ventricle 34 with minimal trauma to the heart. Oxygenated blood is drawn from the left ventricle 34 and routed through passageway 110 to pump 36. The blood is provided by pump 36 via the passageway 40 back through catheter 42 into the ascending aorta to perfuse the body as previously described with regards to FIG. 1, wherein like numerals refer to like elements.

Catheter system 100 facilitates the repair of the aortic valve on the beating heart while providing myocardial infusion. According to the method of the present invention, the valvular repair and replacement of the aortic valve is performed on the beating heart using the catheter system 100 shown in FIG. 4. Catheter system 100 also facilitates performing posterior epicardial revascularization on a beating heart.

Figure 5:
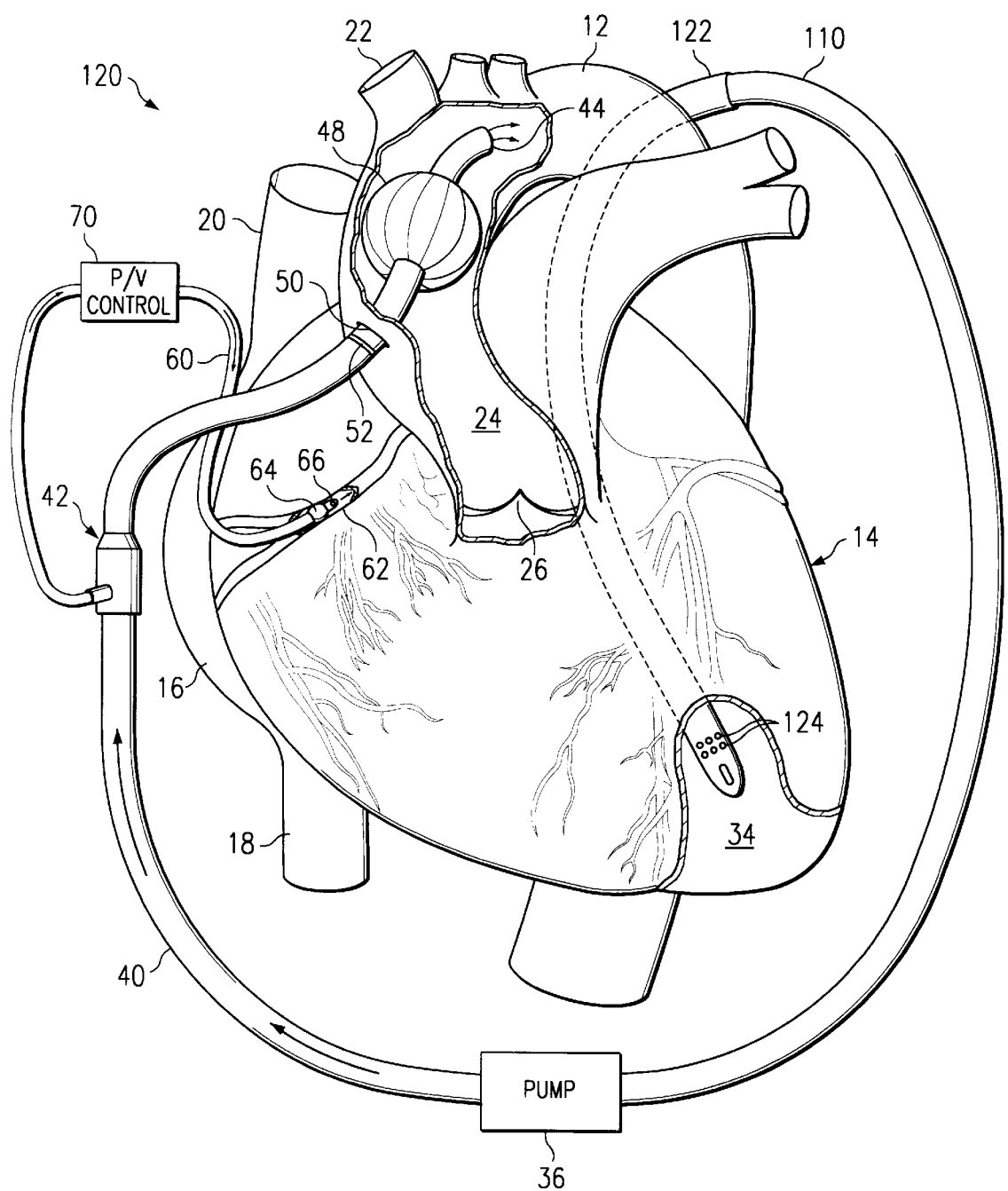
FIG. 5 is an illustration of a third catheter system and method for draining blood from the left ventricle using a catheter inserted through the left atrial apendage and the mitrial valve of the heart for performing aortic valve replacement/repair and epicardial surgery.

Turning now to FIG. 5, there is shown a catheter system and method of use according to a third embodiment of the present invention. In this embodiment, a catheter 122 is inserted into the left atrium 34 via a left atrial apendage and the mitrial valve of the heart, as shown. Blood is drained from the left ventricle 34 via catheter 122 and conduit 110 to pump 36. The drained blood is then returned via the conduit 40 to the aortic perfusion catheter 42 to perfuse the body as previously described with regards to FIG. 1 and FIG. 4, wherein like numerals refer to like elements. Catheter 122 is seen to include a plurality of openings 124 at the distal end thereof draining blood from left ventricle 34 via an interior lumen to conduit 110. Posterior epicardial revascularization as well as intracardiac surgery is facilitated and can be performed on the beating heart.

Figure 6:
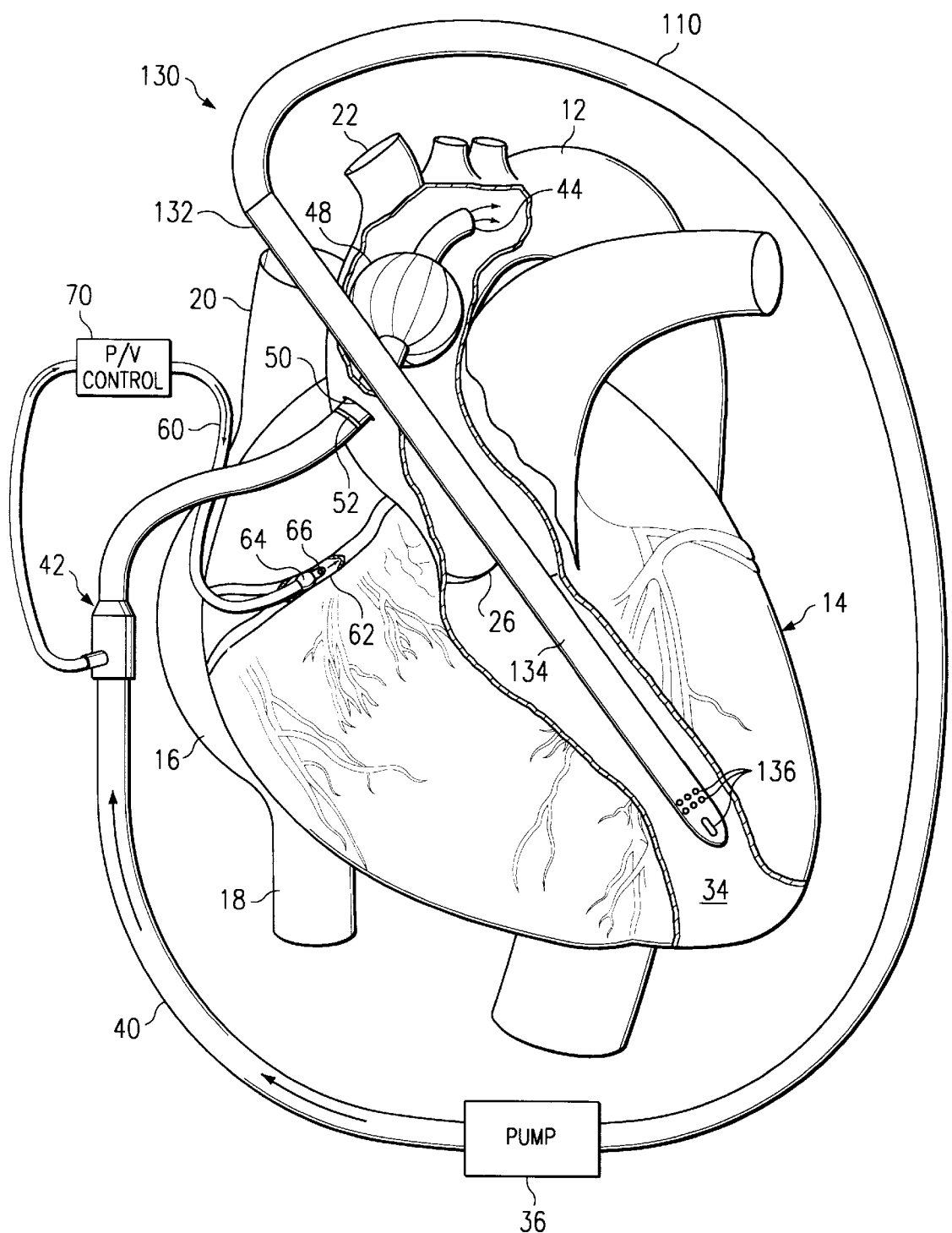
FIG. 6 is an illustration of a fourth catheter system and method for draining the left ventricle of the heart using a catheter inserted through the aorta and the aortic valve of the heart for performing epicardial surgery.

Turning now to FIG. 6, there is shown a catheter system 130 and method of use thereof according to a fourth preferred embodiment of the present invention. In this embodiment, catheter system 130 is seen to include a catheter 132 inserted via an incision into the aorta 12 and advanced through the aortic valve 26 such that the distal end 134 is positioned within the left ventricle 34, as shown. The distal end of catheter 132 is seen to have a plurality of openings 136 for draining oxygenated blood from left ventricle 34 to sufficiently drain all blood therefrom to obtain an left ventricular isolation. Catheter 132 is fluidly connected to passageway 110 which communicates the drained blood to pump 36. Pump 36 pumps the oxygenated blood via the conduit 40 to the aortic perfusion catheter 42 to perfuse the body as previously described wherein like numerals refer to like elements. Catheter 132 is inserted through aorta 12 by forming an suitable incision through the wall thereof proximate the aortic base. Catheter 132 is then carefully inserted through the aortic valve 26 into the left ventricle 34, as shown. In this embodiment, oxygenated blood is adequately drained from left ventricle 34 to obtain an left ventricular isolation without disposing a catheter through the mitrial valve. According to the method of this embodiment, posterior epicardial surgery is facilitated while the heart remains beating. As shown and previously discussed, myocardial perfusion is provided to make sure the myocardium maintains it oxygen demand while the heart remains beating.

Figure 7:
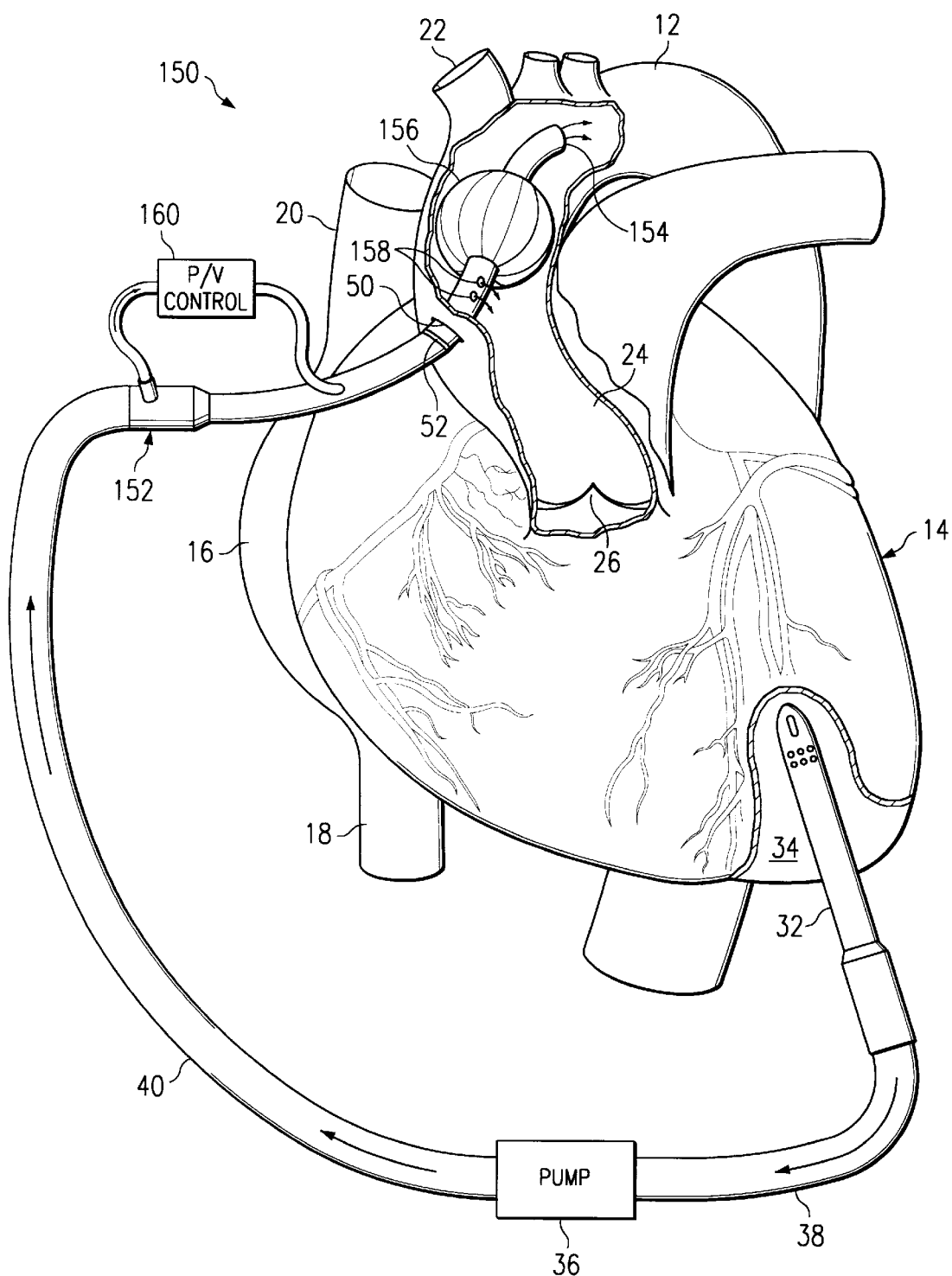
FIG. 7 is an illustration of a fifth catheter system and method for draining the left ventricle of the heart and facilitating epicardial surgery.

Turning now to FIG. 7, there is shown a catheter system 150 and method of use thereof to obtain an left ventricular isolation on a beating heart, similar to the embodiment of FIG. 1, but wherein myocardial infusion is performed in antegrade flow to facilitate posterior epicardial surgery. Catheter system 150 is similar to system 30 of FIG. 1, wherein like numerals refer to like elements. In this embodiment, an aortic perfusion catheter 152 is coupled to the distal end of conduit 40 and provides arterial return to the ascending aorta 12 via the distal end 154 as shown. Catheter 152 has a balloon 156 for controllable and selectively occluding the aorta 12 to perfuse the body similar to balloon 48 of aortic perfusion catheter 42 if it is desired to repair or replace the aortic valve. Balloon 156 may not necessarily be used during posterior epicardial surgery. Catheter 152 is further seen to include a plurality of openings 158 adjacent and proximate the balloon 156 for infusing oxygenated blood into the aortic base 24 to provide myocardial perfusion in antegrade flow during posterior epicardial surgery. It is noted blood is not provided in antegrade flow when replacing/repairing the aortic valve. Catheter 152 is seen to include a pressure/volume control 160 similar to PNv control 70 of FIG. 1 allowing the physician to selectively control the pressure and volume of the antegrade flow of oxygenated blood to the aortic base 24. When providing antegrade flow, the typical volume is 500 milliliters per minute, and a pressure of about 50 mm Hg, both of which can be controlled by the physician using P/V control 160.

Catheter 152 is suitable for use with the other embodiments of FIG. 4, FIG. 5, and FIG. 6 in combination with the various left ventricular catheters to perform posterior epicardial surgery, and valve repair/replacement depending on the configuration. Thus, aortic perfusion catheter 152 is interchangeable with aortic perfusion catheter 42 allowing the physician to customly select whether myocardial infusion is to be performed retrograde or antegrade.

Referring now to FIG. 8, there is shown a partial sectional side view of the aortic perfusion catheter 152 shown in FIG. 7. Catheter 152 is seen to include an inflation lumen 160 extending along the length thereof to a balloon cavity 162 defined by balloon 156. Lumen 160 terminates via an opening 164 into cavity 162. Catheter 152 is further seen to include a large main lumen 170 having a sufficiently large diameter to allow a flow of oxygenated blood at sufficient flow rate and pressure to adequately perfuse the body. Main lumen 170 is seen to terminate at an output port 172 at the distal end 154. At the proximal end of catheter 152 is seen a smaller passageway 176 in communication with main lumen 172 for diverting a small portion of the oxygenated blood flowing through main lumen 170 to the pressure/volume control 160. Lumen 176 extends through a housing finger 178 which angles rearwardly from the connector body 180 as shown. Body 180 is adapted to couple to a balloon inflation source and lumen 40 as shown in FIG. 7. The pressure/volume control 160 communicates the regulated blood flow to a conduit 180, which in turn communicates the blood via lumen 182 into an elongated passageway 184 of catheter 152. Openings 158 communicate the inner lumen 184 with the ambient adjacent and proximal of the balloon 156, as shown. Antegrade infusion of the myocardium is thus facilitated by diverting a small portion of the oxygenated blood from the main lumen 170 to the pressure/volume control 160, and then communicating this diverted blood at a controlled rate and pressure to the inner lumen 184 for dispensing out openings 158 into the aortic base 24 as shown in FIG. 7. The catheter body of catheter 152 is comprised of conventional materials and is sufficiently flexible to allow manipulation within the ascending aorta without creating trauma thereto as shown in FIG. 7.

Figure 9:
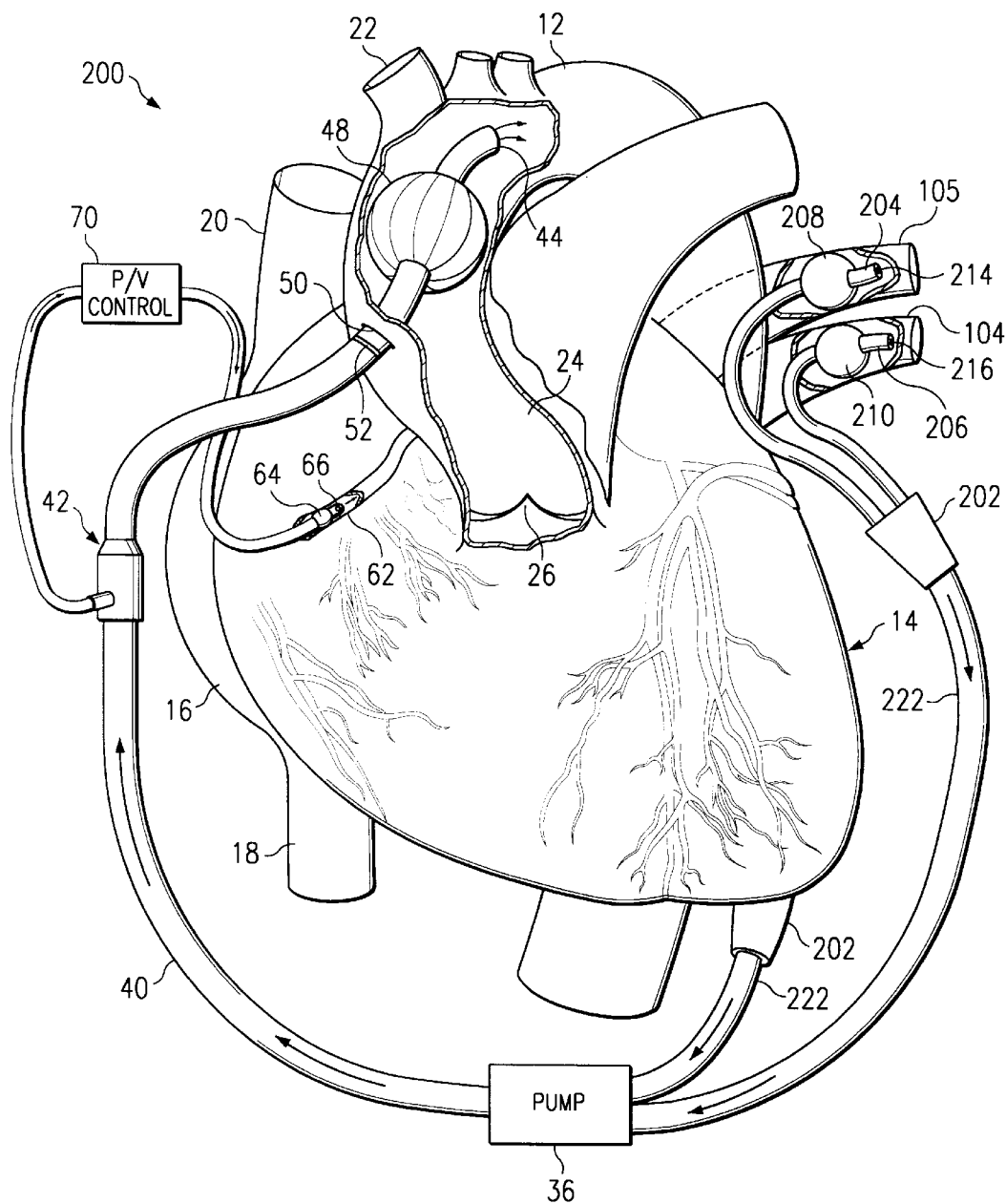
FIG. 9 is an illustration of a sixth catheter system and method for drawing blood from the pulmonary veins to provide a bloodless left ventricle of the heart to facilitate repair or replacement of the mitrial valve and the aortic valve, and perform epicardial surgery.

Referring now to FIG. 9, there is shown a catheter system 200 and method and of use thereof according to a sixth embodiment of the present invention. Catheter system 200 provides an left ventricular isolation of the left ventricle 34 by draining blood returning from the left pulmonary veins 104 and 105, and the right pulmonary veins (not shown). A pulmonary vein catheter 202 includes a pair of distal ends 204 and 206 each adapted to be placed within one of the left pulmonary veins 104 and 105 as shown. A second identical catheter 202 is placed in each of the two right pulmonary veins to draw blood therefrom. Two catheters 202 are thus used in this embodiment and coupled to pump 36. However, a single catheter having four distal ends could be used if desired to drain the left and right pulmonary veins if desired. Distal end 204 is seen to include an occlusion balloon 208, and distal end 206 is seen to include an occlusion balloon 210. Each of the occlusion balloons 208 and 210 are adapted to effectively occlude the respective right and left pulmonary veins. The distal end 204 is further seen to include an opening 214 for draining blood from the left pulmonary vein 105, wherein distal end 206 is seen to include a similar opening 216 for draining blood from the pulmonary vein 104. Openings 214 and 216 fluidly communicate with a combiner valve 220. Combiner valve 220 merges the two conduits to a common output in communication with a passageway 222 extending to pump 36. Pump 36 in turn communicates the drained blood from the two catheters 202 via conduit 40 to the aortic perfusion catheter 42 to perfuse the body as shown, but could also communicate the blood to the aortic perfusion catheter 152 if myocardial infusion is to be provided in antegrade flow if desired.

Catheter system 200 allows returning oxygenated blood from the four pulmonary veins to be directed to the pump 36 before the oxygenated blood actually returns to heart 10, thereby achieving an left ventricular isolation to facilitate a bloodless left ventricle 34. The surgeon can then perform intracardiac surgery, including repair or replacement of the mitrial valve on a beating heart, repair or replace the aortic valve, or provide other posterior epicardial surgical repair to the heart as desired. In summary, catheter system 200 bypasses blood flow around the heart from the four pulmonary veins to the ascending aorta and performs an left ventricular isolation.

Turning now to FIG. 10, there is shown a partial sectional side view of catheter 202. Distal end 204 is seen to include an inner lumen 230 and distal end 206 is seen to include an inner lumen 232. Both lumen 230 and lumen 232 are seen to extend through the respective distal ends and fluidly merge together and communicate with one another at the valve 234 within body 220 as shown. Passageways 230 and 232 merge to form a common passageway 236 extending through passageway 222 and which is adapted to communicate with pump 36 as shown in FIG. 9.

Distal end 204 is further seen to include a balloon inflation lumen 240, whereas distal end 206 is seen to include a balloon inflation lumen 242. Each of the balloon inflation lumens 240 and 242 are in fluid communication with each other and are coupled to a manual inflation device (not shown) for use by the surgeon to selectively inflate the respective balloons 208 and 210. Lumen 240 communicates fluid pressure via opening 244 into cavity 246, whereas lumen 242 communicates fluid pressure via opening 248 into cavity 250, as shown.

Figure 11:
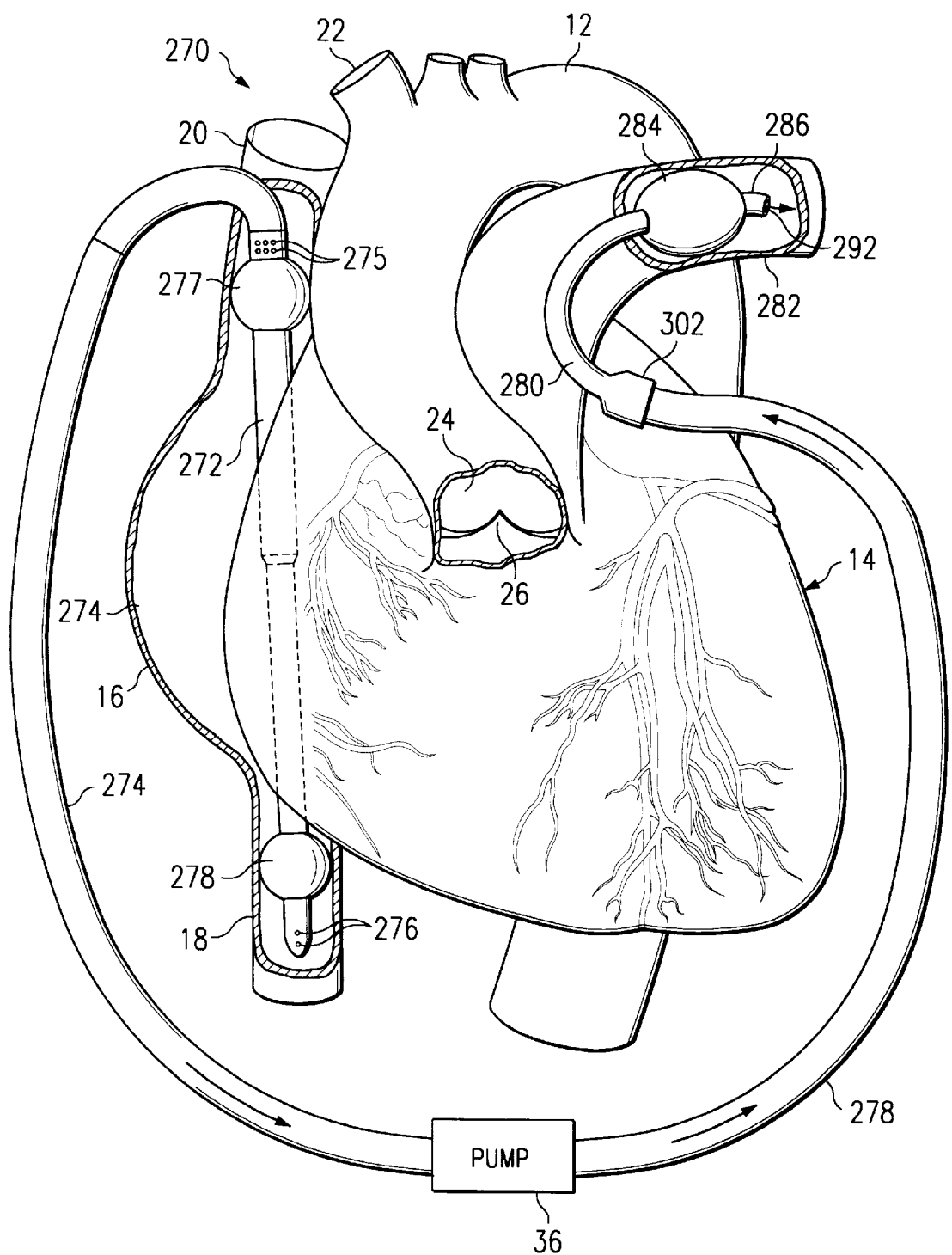
FIG. 11 is an illustration of a seventh catheter system and method providing a right ventricular isolation by draining systemic blood from the superior vena cava and the inferior vena cava, with return blood being directed to the pulmonary artery to facilitate replacement or repair of the pulmonic valve and the tricuspid valve.

Referring now to FIG. 11, there is shown a catheter system 270 and a method use thereof according to a seventh embodiment of the present invention. Catheter system 270 is distinguished from the other embodiments in that catheter system 270 achieves a right ventricular isolation to allow repair or replacement of the pulmonic valve and the tricuspid valve while the heart is beating. This is achieved by draining blood from the inferior vena cava 18 and the superior vena cava 20, as shown, before it enters the right half of the heart 14. The drained systemic blood is directed via a venous return catheter 272 and a passageway 274 to a pump 36. Pump 36 provides the drained blood via conduit 278 to a pulmonary artery catheter 280 for returning the blood to the pulmonary artery 282. Venous return catheter 272 includes a plurality of openings 275 for draining blood from the superior vena cava 20, and a plurality of openings 276 for draining blood from the inferior vena cava 18. Venous return catheter 272 also includes a proximal balloon 277 for occluding the superior vena cava 20 and a distal balloon 278 for occluding the inferior vena cava 18. Openings 275 are proximal of balloon 277, and openings 276 are distal of distal balloon 278.

Pulmonary artery catheter 280 is seen to include an occlusion balloon 284 for selectively and effectively occluding the pulmonary artery 282, and has a distal end 286 for providing arterial return of oxygenated blood into the pulmonary artery as shown. Balloon 284 is selectively inflated by the physician to occlude the pulmonary artery 282 and prevent leakage of blood back into the heart, thereby providing a bloodless right atrium and right ventricle (collectively the right side) of the beating heart. According to the method of this embodiment, the right ventricular isolation is obtained by draining the systemic blood, facilitating posterior epicardial surgery and intracardiac surgery including valvular repair and/or replacement on the beating heart including the pulmonic valve and the tricuspid valve. No myocardial infusion is required according to this method.

It is noted blood could also be drained from the superior vena cava and inferior vena cava using a femorally inserted catheter (not shown), or using a catheter having inflatable balloons to isolate the superior vena cava and the inferior vena cava from the bloodless right atrium, and these procedures are within the scope of the present invention.

Figure 12:
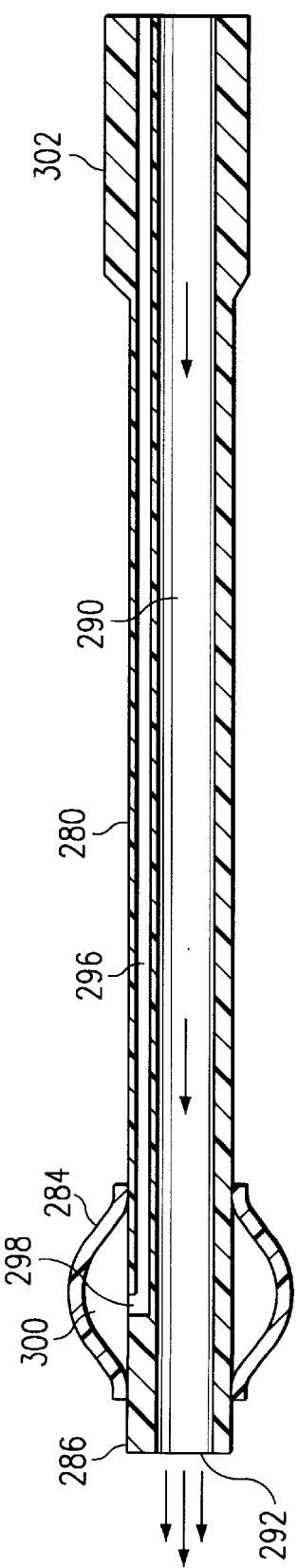
FIG. 12 is a cross section of the pulmonary artery catheter in FIG. 11 providing arterial return to the pulmonary artery.

Turning now to FIG. 12, there is shown a cross sectional view of the pulmonary artery catheter 280 of FIG. 11.

Catheter 280 is seen to include a main infusion lumen 290 having a sufficient diameter to provide an adequate flow of oxygenated blood at a suitable pressure for infusing the pulmonary artery 282 of the body as shown in FIG. 11. Main lumen 290 is seen to terminate at a distal opening 292 which is positioned upwardly into the pulmonary artery as shown in FIG. 11. Catheter 280 is further seen to include a balloon inflation lumen 296 extending therethrough and terminating through an opening 298 into a cavity 300 of balloon 284. The proximal end 302 of catheter 280 is adapted to fluidly couple to conduit 278 whereas balloon lumen 296 is eventually communicated to a manual inflation device controllable by the surgeon to control the inflation of balloon 284. Catheter body 280 is comprised of a suitable flexible material such as silicone, PVC and the like to provide suitable manipulation within the pulmonary artery 282 through an incision made by the surgeon in the artery (not shown).

Figure 13:
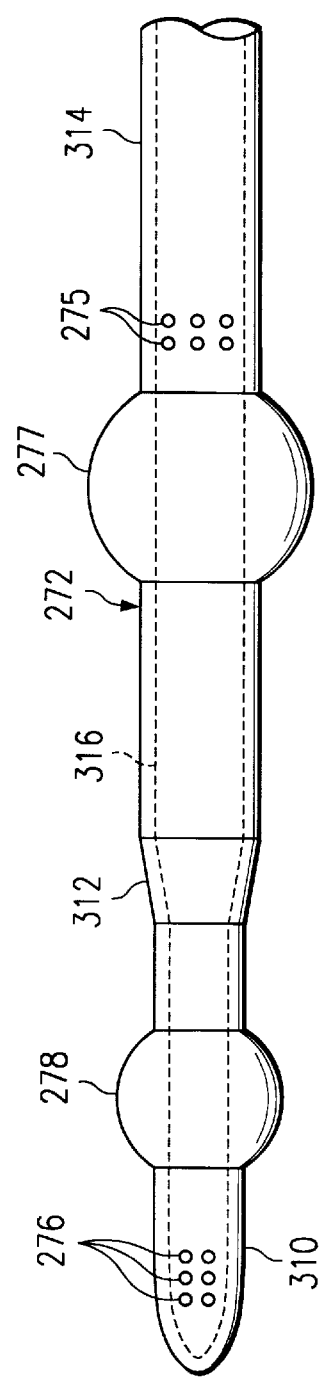
FIG. 13 is a side view of the venous catheter of FIG. 11 for drawing blood from the inferior vena cava and superior vena cava of the heart.

Referring now to FIG. 13, there is shown a side view of the venous return catheter 272 utilized to drain the systemic blood from the superior vena cava and inferior vena cava. Catheter 272 is seen to include a distal portion 310 having a first diameter and the inflatable distal balloon 278, a transition portion 312, and a second proximal portion 314 extending from the transition portion 312 and having a second diameter including distal inflatable balloon 277. The proximal portion 314 has a larger diameter than the proximal portion 310 to facilitate effectively draining blood from the superior vena cava 20. Catheter 272 is comprised of a suitable material such as silicone, PVC and the like to facilitate effective manipulation without kinking. Catheter 272 is further seen to include a lumen 316 extending therethrough in fluid communication with both sets of openings 274 and 276 providing a fluid flow path to the proximal end thereof and conduit 274 as shown in FIG. 11.

In summary, the present invention comprises catheter systems and methods of use thereof for performing posterior epicardial revascularization as well as intracardiac surgery including valvular repair or replacement on a beating heart. Both a left ventricular isolation and an right ventricular isolation can be obtained as required on a beating heart to facilitate the valvular repair and/or replacement, such as repair to the mitrial valve, the aortic valve, the pulmonic valve and the tricuspid valve. Myocardial infusion is provided, either in antegrade flow or retrograde flow as desired, to insure that the myocardium meets its oxygen demand. The catheter system facilitates least invasive cardiac surgery on a beating heart.

Though the invention has been described with respect to a specific preferred embodiment, many variations and modifications will become apparent to those skilled in the art upon reading the present application. It is therefore the intention that the appended claims be interpreted as broadly as possible in view of the prior art to include all such variations and modifications.

We claim:

1. A catheter system for facilitating epicardial surgery and intracardiac surgery on a beating heart having pulmonary veins and an aorta, comprising:
   at least one catheter having a shape and structure adapted to draw blood from the pulmonary veins of the beating heart wherein the at least one catheter has at least two distal ends each adapted to be inserted into one of the pulmonary veins of the heart, wherein each of the distal ends has a balloon having a diameter sufficient to occlude the respective pulmonary vein when inserted therein and a lumen terminating distal of said balloon for drawing blood from the respective pulmonary vein;
   a pump coupled to said first catheter; and
   an aortic catheter coupled to said pump having a lumen and structure adapted to return said drawn blood to the aorta of the beating heart at a sufficient rate and pressure to perfuse the body.

2. A method of performing epicardial revascularization and intracardiac surgery on a beating heart, the heart having a myocardium, an ascending aorta, an aortic base, aortic valve, a left ventricle, a mitrial valve, a coronary sinus, and pulmonary veins comprising a pair of right pulmonary veins and a pair of left pulmonary veins, the method comprising the steps of:
   a) drawing blood from the pulmonary veins using at least one catheter and a pump while said heart is beating to obtain a left ventricular isolation, wherein the at least one catheter has a shape and structure adapted to draw blood from the pulmonary veins of the beating heart wherein the at least one catheter has at least two distant ends each adapted to be inserted into one of the pulmonary veins of the heart, wherein each of the distal ends has a balloon having a diameter sufficient to occlude the respective pulmonary vein when inserted therein and a lumen terminating distal of said balloon for drawing blood from the respective pulmonary vein; and
   b) returning the majority of said drawn blood via said pump to the ascending aorta using an aortic catheter.

3. The method as specified in claim 2 wherein a portion of said drawn blood in said step b) is infused into the myocardium to provide myocardial infusion.

4. The method as specified in claim 2 wherein said portion of said drawn blood is infused into the aortic base to provide antegrade myocardial infusion.

5. The method as specified in claim 3 wherein said portion of said drawn blood is infused into the coronary sinus to provide retrograde myocardial infusion.

6. The method as specified in claim 3 wherein a volume and pressure of said drawn blood is selectively controlled during said myocardial infusion.

7. The method as specified in claim 3 wherein said aortic catheter also infuses said drawn blood into the myocardium.

* * * * *